US008778906B2

(12) United States Patent
Bondarev et al.

(10) Patent No.: US 8,778,906 B2
(45) Date of Patent: *Jul. 15, 2014

(54) MODULATION OF LINE-1 REVERSE TRANSCRIPTASE

(75) Inventors: Igor E. Bondarev, St. Petersburg (RU); John S. Bertram, Honolulu, HI (US)

(73) Assignee: ALT Solutions, Inc., Wilmington, DE (US)

( * ) Notice: Subject to any disclaimer, the term of this patent is extended or adjusted under 35 U.S.C. 154(b) by 920 days.

This patent is subject to a terminal disclaimer.

(21) Appl. No.: 12/070,923

(22) Filed: Feb. 22, 2008

(65) Prior Publication Data
US 2009/0036391 A1 Feb. 5, 2009

Related U.S. Application Data

(63) Continuation of application No. 10/758,329, filed on Jan. 15, 2004, now abandoned.

(60) Provisional application No. 60/440,988, filed on Jan. 15, 2003.

(51) Int. Cl.
*A61K 31/70* (2006.01)

(52) U.S. Cl.
USPC .............................................. 514/45; 514/49

(58) Field of Classification Search
None
See application file for complete search history.

(56) References Cited

U.S. PATENT DOCUMENTS

| | | | |
|---|---|---|---|
| 5,539,082 | A | 7/1996 | Nielsen et al. |
| 5,683,990 | A | 11/1997 | Rideout et al. |
| 5,707,795 | A | 1/1998 | West et al. |
| 5,714,331 | A | 2/1998 | Buchardt et al. |
| 5,719,262 | A | 2/1998 | Buchardt et al. |
| 6,004,939 | A | 12/1999 | Chen et al. |
| 6,046,307 | A | 4/2000 | Shay et al. |
| 6,156,763 | A | 12/2000 | Kerwin et al. |
| 6,194,206 | B1 | 2/2001 | West et al. |
| 6,294,332 | B1 | 9/2001 | Chabot |
| 6,365,578 | B1 * | 4/2002 | Calabresi et al. ............... 514/50 |
| 6,723,712 | B2 | 4/2004 | Bourhis et al. |
| 6,995,145 | B1 * | 2/2006 | Au et al. ........................ 514/43 |
| 7,741,296 | B2 * | 6/2010 | Bondarev ....................... 514/43 |

OTHER PUBLICATIONS (R) Bryan et al. (I), "Evidence for an Alternative Mechanism for Maintaining Telomere Length in Human Tumors and Tumor-derived Cell Lines," Nature Medicine, 3(11), 1271-1274 (Nov. 1997).*
(S) Bryan et al. (II), "Telomere Dynamics and Telomerase Activity in In Vitro Immortalized Human Cells," European Journal of Cancer, 33(5), 767-773 (1997).*
(T) T Kuo et al., "Expression of Transposon LINE-1 is Relatively Human-Specific and Function of the Transcripts May Be Proliferation-Essential," Biochemical and Biophysical Research Comm., 253(3), 566-570 (1998).*
(U) Reddel et al., "Alternative Lengthening of Telomeres in Human Cells," Radiation Research, 155, 194-200 (2001).*
(V) Delap et al., "A Phase I Study of Zidovudine (AZT), Leucovorin (LV), and [5-]Fluorouracil (FU) in Patients with Advanced Cancer," Proc. Annual Meeting of the Amer. Soc. Of Clinical Oncology, 10, p. 106, Abstr. No. 295 (Mar. 1991).*
(W) Doroshow et al., "Phase I Trial of Continuous Infusion Zidovudine (AZT) and Cisplatin in Patients with Advanced Cancer," Proc. Annual Meeting of the Amer. Soc. of Clinical Oncology, 13, p. 146, Abstr. No. 377 (Mar. 1994).*
(X) Gomez et al., "Irreversible Telomere Shortening by 3'-Azido-2',3'-Dideoxythymidine (AZT) Treatment," Biochemical and Biophysical Research Comm., 246(1), 107-110 (1998).*
(Y) Gellert et al., "Telomerase as a Therapeutic Target in Cancer," Drug Discovery Today: Disease Mechanisms, 2(2), 159-164 (2005).*
(Z) Herbert et al., "Telomerase and Breast Cancer," Breast Cancer Research, 3(3), 146-149 (2001).*
(RA) Melana et al., "Inhibition of Cell Growth and Telomerase Activity in Breast Cancer Cells in Vitro by 3'-Azido-3'-deoxythymidine," Clinical Cancer Research, 4, 693-696 (Mar. 1998).*
(SA) Chen et al., "Telomerase Activity in Kaposi's Sarcoma, Squamous Cell Carcinoma, and Basal Cell Carcinoma," Experimental Biology and Medicine, 226(8), 753-757 (2001).*
De Clercq, "Recent developments in the chemotherapy of HIV infections", Pure & Appl. Chem., vol. 70, No. 3, pp. 567-577, 1998.
Yamaguchi, et al., "Telomerase-inhibitory effects of the triphosphate derivatives of some biologically active nucleosides", Nucleic Acids Research Supplement No. 1, pp. 211-212, 2001.
Bisoffi, et al., "Inhibition of Human Telomerase by a Retrovirus Expressing Telomeric Antisense RNA", European Journal of Cancer, vol. 34, No. 8, pp. 1242-1249, 1998.
Roth, et al., "Telomerase is limiting the growth of acute myeloid leukemia cells", Leukemia, 17, pp. 2410-2417, 2003.
Damm, et al., "A highly selective telomerase inhibitor limiting human cancer cell proliferation", The EMBO Journal, vol. 20., No. 24, pp. 6958-6968, 2001.
GeneBank GI:5070620, http://www.ncbi.nlm.nih.gov/entrez/viewer.fcgi?db=nucleotide&val=5070620.
Kimberland, et al., "Full-length human L 1 insertions retain the capacity for high frequency retrotransposition in cultured cells", Human Molecular Genetics, 1999, vol. 8, No. 8, pp. 1557-1560.
Dorafshar, et al., "Vascular Endothelial Growth Factor Inhibits Mitogen-Induced Vascular Smooth Muscle Cell Proliferation", Journal of Surgical Research, 114, pp. 179-186, 2003.

(Continued)

*Primary Examiner* — Lawrence E Crane
(74) *Attorney, Agent, or Firm* — Juan Carlos A. Marquez; Morris, Manning & Martin, LLP

(57) ABSTRACT

A method is provided for treating individuals suffering from cancer characterized by tumor cells which are telomerase negative, do not have telomerase activity or have L1RT expression or alternative lengthening of telomeres. The method includes administering to an individual in need of treatment thereof, and having the aforementioned cancer, a therapeutically effective amount of a nucleoside analog selected from one or more of the group consisting of: 3'-azido-2',3'-dideoxythymidine (AZT), 2',3'-dideoxyinosine (ddI) and 2',3'-didehydro-3'-deoxythymidine (d4T).

27 Claims, 5 Drawing Sheets

(56) References Cited

OTHER PUBLICATIONS

Yang, et al., "Effects of GM-CSF, IL-3, and GM-CSF/ IL-3 fusion protein on apoptosis of human myeloid leukemic cell line Tf-1 induced by irraditiation", Acta Pharmacol Sin Jan. 2004; 25 (1): 68-75.

Schwahn, et al., "Positional cloning of the gene for X-linked retinitis pigmentosa 2", Nature Genetics, vol. 19, Aug. 1998, pp. 327-332.

Holmes, et al., "A new retrotransposable human L1 element from the LRE2 locus on chromosome 1q produces a chimaeric insertion", Nature Genetics, vol. 7, Jun. 1994.

Yoshida, et al., "Insertional mutation by transposable element, L1, in the DMD gene results in X-linked dilated cardiomyopathy", Human Molecular Genetics, 1998, vol. 7, No. 7, pp. 1129-1132.

Brouha, et al., Evidence Consistent with Human L1 Retrotransposition in Maternal Meiosis I, Am J. Hum. Genet. vol. 71, pp. 327-336, 2002.

Atlschul et al., "Gapped BLAST and PSI-BLAST: a new generation of protein database search programs", Nucleic Acids Research, vol. 25, No. 17 pp. 3389-3402, 1997.

Ahlquist, "RNA-Dependant RNA Polymerases, Viruses, and RNA Silencing", Science, vol. 296 pp. 1270-1273, May 17, 2002.

Yeager, et al., "Telomerase-negative Immortalized Human Cells Contain a Novel Type of Promyelocytic Leukemia (PML) Body" Cancer Research, vol. 59, pp. 4175-4179, Sep. 1, 1999.

Rudolph, et al., "Longevity, Stress Response, and Cancer in Aging Telomerase-Deficient Mice", Cell, vol. 96, pp. 710-712, Mar. 5, 1999.

Wang, et al., "Prolonged and Inducible Transgene Expression in the Liver Using Gutless Adenovirus: A Potential Therapy for Liver Cancer", Gastroenterology, vol. 126, pp. 278-289, 2004.

Greider, et al., "Identification of a Specific Telomere Terminal Transferase Activity in Tetrahymena Extracts", Cell, vol. 43, pp. 405-413, Dec. 1985, (Part 1).

Kim, et al., "Specific Association of Human Telomerase Activity with Immortal Cells and Cancer", Science, vol. 266, pp. 2011-2015, Dec. 23, 1994.

Kazazian, Jr., et al., "The impact of L1 retrotransposons on the human genome", Nature Genetics, vol. 19, pp. 19-24, May 1998.

Nozawa, et al., "In vitro expansion of mammalian telomere repeats by DNA polymerase α-primase", Nucleic Acids Research, vol. 28, No. 16, pp. 3117-3124, 2000.

Allshire, et al., "Human telomeres contain at least three types of G-rich repeat distributed non-randomly", Nucleic Acids Research, vol. 17, No. 12, pp. 4611-4627, 1989.

Hahn, et al., "Inhibition of telomerase limits the growth of human cancer cells", Nature Medicine, vol. 5, No. 10, pp. 1164-1170, Oct. 1999.

Bryan, et al., "Telomere elongation in immortal human cells without detectable telomerase activity", The EMBO Journal, vol. 14, No. 17, pp. 4240-4248, 1995.

Gupta, et al., "Development of Retinoblastoma in the Absence of Telomerase Activity", Journal of the National Cancer Institute, vol. 88, No. 16, Aug. 21, 1996.

Dunham, et al., "Telomere maintenance by recombination in human cells", Nature Genetics, vol. 26, pp. 447-450, Dec. 2000.

Clements, et al., "The human LINE-1 reverse transcriptase: effect of deletions outside the common reverse transcriptase domain", Nucleic Acids Research, vol. 26, No. 15, pp. 3528-3535, 1998.

Skowronski et al., "Expression of a cytoplasmic LINE-1 transcript is regulated in a human teratocarcinoma cell line", Proc. Natl. Acad. Sci. USA, vol. 82, pp. 6050-6054, Sep. 1985.

Moran et al., "High Frequency Retrotransposition in Cultured Mammalian Cells", Cell, vol. 87, pp. 917-927, Nov. 29, 1996.

Murakami, et al., Inhibition of Telomerase Activity and Cell Proliferation by a Reverse Transcriptase Inhibitor in Gynaecological Cancer Cell Lines, European Journal of Cancer, vol. 35, No. 6, pp. 1027-1034, 1999.

Rufer, et al., "Telomere length dynamics in human lymphocyte subpopulations measured by flow cytometry", Nature Biotechnology, vol. 16, p. 743-747, Aug. 1998.

Hultdin, et al., "Telomere analysis by fluorescence in situ hybridization and flow cytometry", Nucleic Acids Research, vol. 26, No. 16, pp. 3651-3656, 1998.

Perrem, et al. "Repression of an alternative mechanism for lengthening of telomeres in somatic cell hybrids", Oncogene, vol. 18, pp. 3383-3390, 1999.

Guiducci, et al., "Expression of mutant telomerase in immortal telomerase-negative human cells results in cell cycle deregulation, nuclear and chromosomal abnormalities and rapid loss of viability", Oncogene, vol. 20, pp. 714-725, 2001.

Craig, et al., "Effects of adenovirus-mediated p16$^{INK4A}$ expression on cell cycle arrest are determined by endogenous p16 and Rb status in human cancer cells", Oncogene, vol. 16, pp. 265-272, 1998.

Ostertag, et al., "Determination of L 1 retrotransposition kinetics in cultured cells", Nucleic Acids Research, vol. 28, No. 6, pp. 1418-1423, 2000.

Hernandez, et al., "Systemic treatment modalities in the management of AIDS-related Kaposi's sarcoma", Journal of the European Academy of the Dermatology and Venereology, 9, 1997, pp. 44-49.

Poirier, et al., "Perinatal genotoxicity and carcinogencity of anti-retroviral nucleoside analog drugs", Toxicology and Applied Pharmacology, 199, 2004, pp. 151-161.

Langford, et al., Regression of oral Kaposi's sarcoma in a case of AIDS on Zidovudine (AZT), British Journal of Dermatology, vol. 120, 1989, pp. 709-713.

Ofelia, et al., "Transplacental Effects of 3'-Azido-2', 3'-Dideoxythymidine (AZT): Tumorigenicity in Mice and Genotoxicity in Mice and Monkeys", Journal of the National Cancer Institute, vol. 89, No. 21, Nov. 5, 1997, pp. 1602-1618.

Pluda, et al., "Parameters Affecting the Development of Non-Hodgkin's Lymphoma in Patients With Severe Human Immunodeficiency Virus Infection Receiving Antiretroviral Therapy", Journal of Clinical Oncology, vol. 11, No. 6, Jun. 1993, pp. 1099-1107.

Giordano, et al., "Reverse Transcriptase Activity in Mature Spermatozoa of Mouse", The Journal of Cell Biology, vol. 148, No. 6, Mar. 20, 2000, pp. 1107-1113.

Mangiacasale, et al., "Exposure of normal and transformed cells to nevirapine, a reverse transcriptase inhibitor, reduces cell growth and promotes differentiation", Oncogene, vol. 22, 2003, pp. 2750-2761.

Beraldi, et al, "Expression of LINE-1 Retroposons is Essential for Murine Preimplantation Development", Molecular Reproduction and Development, vol. 73, 2006, pp. 279-287.

Soifer, et al., "A potential role for RNA interference in controlling the activity of the human LINE-1 retrotransposon", Nucleic Acids Research, vol. 33, No. 3, 2005, pp. 846-856.

Sciamanna, et al., "Inhibition of endogenous reverse transcriptase antagonizes human tumor growth", Oncogne, vol. 24, 2005, pp. 3923-2931.

Strahl et al. (1996) Molecular and Cell Biology 16:53-65.

Gan et al. (2002) FEBS Lett. 527:10-14.

Bocchetta et al. (2004) Oncogene 23:6484-6491.

Chabner et al. (2005) Nature Reviews Cancer 65-72.

Mathias et al. (1991) Science 254: 1808-1810.

Wagner et al. (1997) Cancer Res. 57:2341-5.

Hernandez and Perez (1997) J. Eur. Acad. Dermatol. Vener. 9:44-49.

Wagner, C.R., et al., "Potent Growth Inhibitory Activity of Zidovudine on Cultured Human Breast Cancer Cells and Rat Mammary Tumors", Cancer Research, American Association for Cancer Research, US, vol. 57, No. 12, Jun. 15, 1997, pp. 2341-2345, XP008123001; ISSN: 0008-5472; Abstract.

Mo, Yiqun, et al., "Simultaneous Targeting of Telomeres and Telomerase as a Cancer Therapeutic Approach", Cancer Research, vol. 63, No. 3, Feb. 1, 2003, pp. 579-585, XP8125050; ISSN: 0008-5472; Abstract.

Gan, Yuebo, et al., "Telomere maintenance in human ovarian SKOV-3 cells is independent of telomerase and alternative lengthening of telomere", Proceedings of the Annual Meeting of the American Association for Cancer Research, US, vol. 43, Mar. 1, 2002, p. 302, XP001537364; ISSN: 0197-016X; Abstract.

(56) References Cited

OTHER PUBLICATIONS

Mokbel, K, "The evolving role of telomerase inhibitors in the treatment of cancer", Current Medical Research and Opinion 2003, GB LNKD—DOI: 10.1185/030079903125002081, vol. 19, No. 6, 2003, pp. 470-472, XP008125148; ISSN: 0300-7995; Abstract; p. 471, col. 1, paragraph 2.

Izbicka, Elzbieta, et al., "Telomere-interactive agents affect proliferation rates and induce chromosomal destabilization in sea urchin embryos", Anti-Cancer Drug Design, vol. 14, No. 4, Aug. 1999; pp. 355-365; XP008125153; ISSN: 0266-9536; Abstract; Introduction; AZT; p. 359, col. 2; p. 361, col. 2, paragraph 3—p. 364, paragraph 1; p. 364, col. 2, paragraph 1.

* cited by examiner

MODULATION OF LINE-1 REVERSE TRANSCRIPTASE

CROSS REFERENCE TO RELATED APPLICATIONS

This application claims the benefit of U.S. Provisional Patent Application No. 60/440,988 filed Jan. 15, 2003, and the text of application 60/440,988 is incorporated by reference in its entirety herewith, and U.S. patent application Ser. No. 10/758,329 filed Jan. 15, 2004.

FIELD OF THE INVENTION

The present invention is directed to the field of cancer therapy. Specifically, target molecules have been identified modulation of which regulates elongation of telomeres in telomerase negative cancerous cells. More particularly, it relates to the use of various inhibitor compounds that interfere with human L1 (Line-1) retrotransposon encoded reverse transcriptase (L1RT) for treating or preventing L1RT induced cancers. The invention also relates to screening methods for identifying pharmacologically active compounds that may be useful for treating L1RT-mediated proliferative diseases.

BACKGROUND OF THE INVENTION

An asymmetry in the synthesis of leading and lagging DNA strands creates the "end problem" for replication of linear genomes[8]. To overcome this, eukaryotic chromosomes have specialized end structures, telomeres, consisting of TTAGGG repeats[9]. Telomerase is a ribonucleoprotein enzyme that elongates telomeres and therefore maintains chromosomal stability in majority of cancer cells during cell doubling. The gradual loss of DNA from the ends of telomeres during cell doubling has been implicated in the control of cellular proliferative potential in somatic cells[10].

Normal cultured human cells have a limited replication potential in culture. As was first described by Hayflick, normal cells in culture replicate until they reach a discrete point which population growth ceases. This is termed M1 stage and is caused by the shortening of a few telomeres to a size that leads to a growth arrest called cellular senescence. This stage can be bypassed in vitro by abrogation of the function of p53 and pRB human tumor suppressor genes. The cells then can proliferate until the telomeres have become critically shortened, which produces the M2 or crisis stage. The growth arrest in the M2 stage is caused by balance between the cell proliferation and cell death rate. At this stage, when most of telomeres are extremely short, end-to-end fusions and chromosomal breakage-fusion cause marked chromosomal abnormalities and apoptosis. Under rare circumstances, a cell can escape M2 and become immortal by stabilizing the length of its telomeres. This occurs through the activation of the enzyme telomerase or an alternative mechanism of telomere lengthening (ALT).

Human germline[2] and the majority of cancer cells[3] express telomerase. Telomerase is a ribonucleoprotein enzyme that elongates telomeres and, therefore, maintains chromosomal stability in majority of cancer cells during cell doubling. Indeed, elongation of shortened telomeres by telomerase is a major mechanism of telomere maintenance in the human cancer cells. Inhibition of telomerase limits the growth of human telomerase positive cancer cells[11] by decreasing telomere length, these compounds diminish the ability of these cancer cells to proliferate. Reverse transcriptase inhibitors have been used previously to treat cancer. In in vitro tests, tumor cells treated with the reverse transcriptase inhibitors underwent apoptosis after 14 days.

Elongation of shortened telomeres by telomerase is a well known mechanism of telomere maintenance in the human cancer cells. However up to 30% of human tumors of different types do not express telomerase. The presence of ALT was reported in up to 30% of human tumors of different types, tumor-derived cell lines and human cell lines immortalized in vitro[4,5,12,13], and up to 50% in some subsets of tumors and immortalized cell lines[14].

Currently, strategies aimed at selectively treating the cancers from telomerase positive cells involve modulation of TERT function or length of telomeres by antisense strategy, dominant negative mutants or pharmacological agents (see, Bisoffi et al., Eur J Cancer, 1998, 34:1242-1249; Roth et al., Leukemia, 2003, 17:2410-2417; Damm et al., EMBO J., 2001, 20:6958-6968; U.S. Pat. Nos. 6,294,332, 6,194,206, 6,156,763 and 6,046,307). Selective modulation (i.e., selective inhibition or promotion) of telomerase negative cancer cells may also be made possible if the target molecule(s) responsible for the lengthening of telomeres in such cells are known. Thus, there is need for identifying target molecules responsible for the lengthening of telomeres in telomerase negative cells and identifying agents for selectively interfering with the identified target molecules so that human tumors of types that do not express telomerase may also be prevented or treated.

SUMMARY OF THE INVENTION

It has now been found that a product of L1 (Line-1) retrotransposon reverse transcriptase nucleic acid is associated with the lengthening and therefore maintenance of telomeres in certain cancer cells. Specifically, it has been found that interference with the expression of reverse transcriptase encoded by the L1 retrotransposon suppresses the elongation of telomeres in the cancer cells. More specifically, it has been found that interference with the expression of the L1 reverse transcriptase in telomerase negative cells leads to phenotypic manifestations such as telomere shortening, cell cycle arrest and apoptosis or cell death. It is believed that the reverse transcriptase is involved in maintaining telomeres probably by "slippage" mechanism of telomeric DNA synthesis and/or telomere end targeted L1 transposon retrotransposition.

Still more specifically, it has been found that treatment of the telomerase negative cells (ALT cells) with reverse transcriptase inhibitor 3'-azido-2',3'-dideoxythymidine (AZT) or suppression of L1 reverse transcriptase (L1RT) using antisense strategy induces progressive telomere loss, G2 phase arrest, chromosomal abnormalities and eventual cell death.

Accordingly, in one embodiment of the invention, a method is provided for treating tumors characterized by expression of L1RT and/or absence of telomerase expression. Interference with L1RT expression or activity will either directly result in cell death or will potentiate the effects of chemotherapeutic agents that ultimately kill cells through apoptosis. In particular, the invention provides a method for inhibiting proliferation of L1RT expressing cells having potential for continuous increase in cell number by administering inhibitors and antagonists of L1RT. For example, L1RT expression can be suppressed or down regulated by obtaining a DNA molecule having a cDNA sequence operably linked to a promoter such that it will be expressed in antisense orientation, the cDNA having all or part of the sequence of L1RT, and transfecting, with the DNA molecule, the L1RT cells with potential for uncontrolled proliferation. The inhibitor or antagonist is optionally administered with a pharmaceutically acceptable carrier.

In another embodiment of the invention, a method for prevention of a cancer in a person (e.g. a human) in need thereof is provided. The cancer is due to the presence in the human of cells showing alternative lengthening of telomeres induced or mediated by L-1 (LINE-1) retrotransposon encoded reverse transcriptase in the cells of the person. Lengthening of telomeres in cells induces a potential for continuous proliferation of such cells in the human body. The preventive method involves administration of a therapeutically effective amount of a composition to the person. The composition has an inhibitor or antagonist of the reverse transcriptase. The inhibitor or antagonist blocks lengthening of telomeres in telomerase negative cells thereby inhibiting proliferation of L1RT expressing cells having potential for continuous increase in cell number. Preferably the inhibitor is one or more nucleoside analogs, or a pharmaceutically acceptable salt of such analogs. A liquid or solid food material is enriched with inhibitor or antagonist. The food product can be, for example, a functional food in the form of butter, margarine, biscuits, bread, cake, candy, confectionery, yogurt or another fermented milk product, or cereal suitable for consumption by humans. Alternatively, it can be a nutritional supplement, a nutrient, a pharmafood, a nutraceutical, a health food and/or a designer food. Periodically, the human is tested for the presence of ALT cells. The use of inhibitor or antagonist may be stopped once the ALT cells are no longer detected.

In another embodiment of the invention, a method is provided for screening candidate drugs or compounds to select drugs with potential for decreasing the rate of accumulation of tumor cells by incubating or treating cells expressing L1RT with a candidate drug and monitoring one or more desired biological effects the candidate drug(s) may have on the cells. If the candidate drug causes a desired biological effect, then the drug is selected. Particularly preferred biological effects in such a screening include progressive telomere loss, G2 phase arrest, chromosomal abnormalities or cancer cell death. The biological effects may also include inhibition of proliferation of telomerase negative cells transformed with various oncogenes such as, for example, ras.

The invention further provides methods and kits for detecting pathologically proliferating cells expressing L1RT. These and other embodiments of the invention will be described in more detail below.

DETAILED DESCRIPTION OF THE INVENTION

Figure 1:
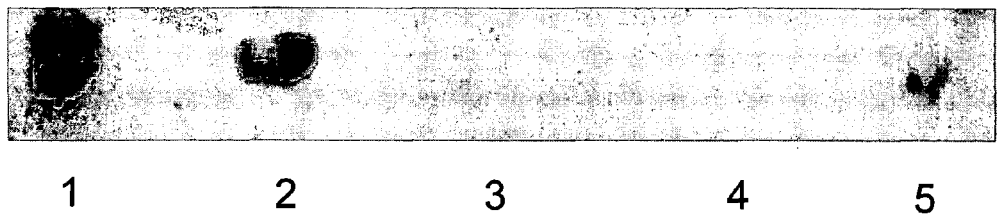
FIG. 1 is a dot blot of total cellular RNA from ALT and telomerase positive cell lines with telomere specific probe. 1, U-2 OS. 2, Saos-2. 3, no RNA. 4, HEC-1. 5, HeLa.

The present invention discloses that LINE-1 (L1) retrotransposon encoded reverse transcriptase (L1RT) enzyme is involved in lengthening of telomeres in certain human cancer cells. Specifically, the present invention discloses that L1RT is involved in lengthening of telomeres in certain tumor tissues including telomerase negative tumors and the tumor-derived cell lines, and identifies L1RT enzyme or the sequences encoding it as a target for controlling the proliferative properties of the tumor cells or inducing apoptosis of these cells.

The telomerase negative tumors and the tumor-derived cell lines are those that do not express or have the endogenous telomerase and yet show lengthening of telomeres, also referred to herein as alternative lengthening of telomeres (ALT). The L1RT mediated telomere lengthening in cells can be characterized by the presence of long and heterogeneous telomeres relative to the telomere lengthening mediated by telomerase. One skilled in the art would know how to determine the presence of long and heterogeneous telomeres characteristic of ALT in cells by carrying out, for example, TRF assay (see, Bryan et al., 1997, Nature Medicine, 3:1271-1274).

L1 reverse transcriptase, which is encoded by ORF2 of L1 retrotransposon, has already been characterized and its nucleic acid and protein sequences are known in the art (GeneBank GI: 5070620; Ostertag et al., 2000, Determination of L1 retrotransposition kinetics in cultured cells, *Nucleic Acids Res.* 28, 1418-1423; Kimberland et al., 1999, Full-length human L1 insertions retain the capacity for high frequency retrotransposition in cultured cells, *Hum. Mol. Genet.* 8 (8), 1557-1560). In the present invention, it has been discovered that L1RT adds telomeric DNA repeats to chromosomes in telomerase negative cells.

Accordingly, in an aspect of the present invention, methods for preventing or treating disorders caused by the presence of inappropriately or pathologically proliferating cells or immortal cells in animals are provided. The inappropriately or pathologically proliferating cells or immortal cells exist and reproduce independently of cells' normal regulatory mechanisms. These cells are pathologic because they deviate from normal cells as a result of activity of a cellular element, i.e., L1RT. Of course, the inappropriately proliferating cells as used herein may be benign hyperproliferating cells but unless stated otherwise these cells refer to malignant hyperproliferating cells such as cancer cells characteristic of, for example, osteosarcoma, breast carcinoma, ovarian carcinoma, lung carcinoma, adrenocortical carcinoma or melanoma.

In particular, methods for preventing or treating human tumors characterized as expressing L1RT are provided. The prevention or treatment of the disorders, according to the present invention, are achieved by the utilization of inhibitors or antagonists of L1RT. The inhibitor(s) or antagonist(s) used in the present invention are those that directly or indirectly interact with L1RT to inhibit its expression (or activity) and/ or those that get incorporated into telomere and thus prevent telomere from further elongation despite the functional L1RT thereby inhibiting the growth of cells expressing L1RT. Thus, the inhibitors or antagonists of L1RT are used for inhibiting the growth of cells. For example, when the inhibitors or antagonists of L1RT are administered to a patient, these cause progressive telomere shortening, cell cycle arrest in the cells and/or massive apoptosis of the cells expressing L1RT. In the present invention, inhibiting the growth may also mean reducing or preventing cell division. Inhibition of growth of cells expressing L1RT, in the present invention, may be about 100% or less but not 0%. For example, the inhibition may be from about 10% to about 100%, preferably at least about 25%, and more preferably at least about 50%, still more preferably at least about 90%, 95% or exactly 100% compared to that of the control cells (control cells express L1RT but are not treated with an inhibitor or antagonist). The inhibition of growth can be measured by any methods known in the art. For example, viable cell number in treated samples can be compared with viable cell number in control samples, determined after incubation with vital stains. In addition, growth inhibition can be measured by assays that can detect reductions in cell proliferation in vitro or in vivo, such as tritiated hydrogen incorporation assays, BdU incorporation assay, MTT assay, changes in ability to form foci, anchorage dependence or losing immortalization, losing tumor specific markers, and/or inability to form or suppress tumors when injected into animal hosts (Dorafshar et al., 2003, J Surg Res., 114:179-186; Yang et al., 2004, Acta Pharmacol Sin., 25:68-75).

The development of a cancerous tumor from a single immortalized cell or few such cells may take several months to years in humans. By practising the present invention, however, cancer can be prevented because the ability of the tumorigenic ALT cells treated with L1RT inhibitors lose their proliferative potential before they have had a chance to grow into a tumor. Further, periodic preventative administration of L1RT inhibitors or antagonists to at risk groups in order to stop tumor progression before clinical manifestation of cancer could potentially decrease the rate of new cancer cases significantly.

The inhibitor or antagonist of the L1RT used in the present invention can be an inorganic compound, an organic compound, an antisense sequence, a double-stranded RNA (dsRNA) corresponding to a defined target region in L1RT mRNA, a dominant negative mutant of the L1RT protein, an antibody or a small molecule.

In one embodiment of the invention, organic compounds such as, for example, nucleoside analogs are used as inhibitors or antagonists of L1RT. Thus, one of the approaches for targeting L1RT is by administration of nucleoside analog(s) to cancer patients. The nucleoside analogs can mimic the building blocks used by L1RT to extend the chromosomal ends in telomerase negative cells. These fake building blocks (i.e., nucleoside analogs) that are incorporated into chromosomal ends by L1RT may interfere with the function of the telomeres and thereby contributing to telomere shortening, cell cycle arrest and cell death.

There are a number of nucleoside analogs known to one skilled in the art. Indeed, nucleoside analogues are known class of antiretrovirals and a number of nucleoside analog drugs have been approved for the treatment of HIV infected humans. These drugs do stop HIV from multiplying by interfering with copying HIV's genetic material (RNA) into the form of DNA. Examples of nucleoside analogues that may be used in the present invention are, 3'-azido-2',3'-dideoxythymidine (AZT), 2',3'-dideoxyinosine (ddI) and 2',3'-didehydro-3'-deoxythymidine (d4T). The other known nucleoside analogues such as Dideoxycytidine (ddC) and 3TC may be used in some situations as determined by one skilled in the art.

Since L1RT is a key factor in cancers of telomerase negative cells, the present discovery of noncompetitive inhibitors of the activity of this key enzyme represents a potential breakthrough in cancer research and treatment. The demonstration that nucleoside analogs (e.g., AZT) clearly block ALT cancer in a widely accepted model systems (described below), confirms that the present invention truly represents a dramatic breakthrough. Although not suggesting the advantageous uses made possible by this invention, the previous administration of AZT to AIDS patients means that AZT can be readily administered to cancer patients.

Indeed, nucleoside analogs have been used to modify telomerase activity in cancer cells to levels close to that found in normal cells as a means for cancer therapy. The concentration of nucleoside analogs required to inhibit L1RT, however, can be several fold lower than that required to inhibit telomerase. For example, the concentration of AZT required for inhibiting L1RT activity can be orders of magnitude lower (e.g., 10 to 1000 fold lower) than that required for inhibiting telomerase activity. The susceptibility of L1RT to such low levels of nucleoside analogs is quite unexpected and this unexpected finding now offers an advantageous avenue of therapy for treatment of L1RT specific cancers. Importantly, the present invention provides for the selection of effective doses significantly lower than the levels that may otherwise be used in cancer patients. The studies of this invention indicate that AZT will be useful in cancer at levels that achieve nanomolar drug levels rather than 200 μM to 800 μM.

Further, the present use of nucleoside analogs to AIDS patients, coupled with the ability to use significantly lower doses of AZT for HIV therapy, should speed regulatory approval for the use of AZT in the treatment of L1RT induced and/or mediated cancers. Moreover, this invention is not limited to the use of AZT to treat L1RT induced and/or mediated cancers. In fact, the use of L1RT inhibitors is broadly applicable to a range of other disorders in which L1RT is a factor. These include, for example, L1 induced mutations in the gene for blood factor VIII inducing hemophilia A, in the X-linked retinitis pigmentosa 2, in the dystrophin gene, in the DMD gene resulting in X-linked dilated cardiomyopathy and in the X-linked gene CYBB causing chronic granulomatous disease (Woods-Samuels et al., 1989, Genomics, 4:290-296; Schwahn et al., 1998, Nat. Genet., 19:327-332; Holmes et al., 1994, Nat Genet., 7:143-148; Yoshida et al., 1998, Hum Mol Genet., 7:1129-1132; Brouha et al., 2002, Am J Hum Genet., 71:327-336).

The nucleoside compounds may be administered either singly or in combinations of different analogs and by any routes of administration, including oral administration. AZT is a preferred nucleoside analog. AZT is commercially available and AZT formulations are described in a number of U.S. patents. See, for example, U.S. Pat. No. 5,683,990. The cells with ALT will be selectively targeted because these cells depend on L1RT for elongating or maintaining telomeres and the elongation or maintenance of telomeres requires the incorporation of the nucleosides and/or their analogs. To the extent any specific targeting agent is desired for delivering the analogs to exert anti-cancer effects, the use of targeted AZT and/or other analogs are contemplated herein. Accordingly, in some embodiments, pharmaceutical compositions may have the active compound, in this case, AZT or a other nucleoside analog, which has been conjugated to a targeting agent (e.g., a peptide) for specific delivery to particular target cells or to nuclear portion within cells.

In another aspect of the invention antisense sequence(s), also referred to herein as antisense oligonucleotide(s) or antisense polynucleotide(s) are used as inhibitors or antagonists of L1RT. The antisense sequences in the present invention are either substantially or fully complementary to a nucleic acid encoding L1RT. The complementarity (whether full or substantial complementarity) of the antisense sequences is such that they specifically hybridize with the target nucleic acid sequence and interfere with L1RT function, expression or otherwise, and the interference is sufficient to inhibit the growth of the cells.

The nucleic acid encoding L1RT can be DNA, RNA transcribed from such DNA or a cDNA of the RNA. The L1 nucleic acid and amino acid sequences of various mammals, such as mouse, monkey and humans have been sequenced (see GenBank Accession numbers AY053456, AF036235, AF148856 and GI5070620) (see also, GenBank protein accession AAD39215 for L1RT ORF2 sequence). In the context of the present invention, L1RT mRNA is a preferred nucleic acid for which antisense nucleic acid sequences are designed. For example, a series of antisense phosphorothioate oligonucleotides, 20 or more nucleotides in length, targeting the nucleic acid encoding L1RT are designed. Generally, the antisense sequences in the present invention may be designed to bind to the promoter or other control regions and coding and/or non-coding regions of L1RT. The antisense sequences preferably target L1RT nucleic acid sequence portion encompassing a start codon. It is also contemplated that the most effective antisense sequences or constructs will include regions complementary to coding and non-coding regions of L1RT. One can readily test the effectiveness of a given antisense construct simply by testing the construct in vitro to determine whether normal cellular function is affected. It is preferred that the selected antisense sequence inhibits L1RT activity or expression to the level that is insufficient for inducing or mediating telomere lengthening in ALT cells.

Interference with L1RT expression can happen due to any mechanism. For example, it is believed that such antisense sequences bind to, and interfere with the translation of, the sense L1RT mRNA. Alternatively, the antisense sequence may render the L1RT mRNA susceptible to nuclease or ribozyme digestion, interfere with transcription, or interfere with processing of L1RT mRNA, repress transcription of mRNA from the L1RT gene, or act through some other mechanism, e.g., through ribozymes. Ribozymes, which are well known to those skilled in the art, are molecules of RNA that have catalytic activity. The ribozymes of the invention are antisense sequences that bind and enzymatically cleave and inactivate L1RT RNA. Useful ribozymes can comprise 5'- and 3'-terminal sequences complementary to the L1RT RNA and can be engineered by one of skill on the basis of the L1RT RNA sequence. However, the particular mechanism by which the antisense sequences interfere with L1RT expression is not critical so long as the end result is met.

Generally, to assure specific hybridization, the antisense sequence is substantially complementary to the target L1RT mRNA sequence. In certain embodiments, an antisense sequence that is fully or exactly complementary to the target nucleic acid sequence or two or more antisense sequences fully complementary to different subsequences of a given L1RT target nucleic acid sequence may be used. A Subsequence is a sequence of nucleic acid residues or nucleotides that is a part of a longer sequence of nucleic acid residues such as, for example, an antisense sequence corresponding to nucleotides 1987-2800 of human L1 reprotransposon (GenBank GI: 5070620).

TABLE

Exemplary sequences for use in interfering with L1RT mRNA.

| SEQ ID NO: | Nucleic Acid Sequence |
| --- | --- |
| SEQ ID NO:1 (a sequence antisense to L1RT mRNA results when the sequence set forth herein, SEQ ID NO:1, in reverse orientation, is expressed in an expression vector) | 5'-atga caggatcaac ttcacacata acaatattaa cttttaaatat aaatggacta aattctgcaa ttaaaagaca cagactggca agttggataa agagtcaaga cccatcagtg tgctgtattc aggaaaccca tctcacgtgc agagacacac ataggctcaa aataaaagga tggaggaaga tctaccaagc caatggaaaa caaaaaaagg caggggttgc aatcctagtc tctgataaaa cagactttaa accaacaaag atcaaaagag acaaagaagg ccattacata atggtaaagg gatcaattca acaagaggag ctaactatcc taaatattta tgcacccaat acaggagcac ccagattcat aaagcaagtc ctcagtgacc tacaaagaga cttagactcc cacacattaa taatgggaga ctttaacacc ccactgtcaa cattagacag atcaacgaga cagaaagtca acaaggatac ccaggaattg aactcagctc tgcaccaagc agacctaata gacatctaca gaactctcca ccccaaatca acagaatata catttttttc agcaccacac cacacctatt ccaaaattga ccacatagtt ggaagtaaag ctctcctcag caaatgtaaa agaacagaaa ttataacaaa ctatctctca gaccacagtg caatcaaact agaactcagg attaagaatc tcactcaaag ccgctcaact acatggaaac tgaacaacct gctcctgaat gactactggg tacataacga aatgaaggca gaaataaaga tgttctttga aaccaacgag aacaaagaca ccacatacca gaatctctgg gacgcattca aagcagtgtg tagagggaaa tttatagcac taaatgccta caagagaaag cagga-3' |
| SEQ ID NO:2 (a sequense antisense to a portion of L1RT mRNA) | 5'-CCA GAG ATT CTG GTA TGT GGT GTC TTT GTT-3' |
| SEQ ID NO:3 (a sequense antisense to a portion of L1RT mRNA) | 5'-CTT TCT CTT GTA GGC ATT TAG TGC TAT AAA-3' |
| SEQ ID NO:4 (a sequense antisense to a portion of L1RT mRNA) | 5'-CTC TTG CTT TTC TAG TTC TTT TAA TTG TGA-3' |
| SEQ ID NO:5 (a sequense antisense to a portion of L1RT mRNA) | 5'-CTT CAG TTC TGC TCT GAT TTT AGT TAT TTC-3' |
| SEQ ID NO:6 (a sequense antisense to a portion of L1RT mRNA) | 5'-TCC TGC TTT CTC TTG TAG GCA-3' |

The antisense sequences, e.g., DNA, RNA, modified, analogues or the like can be made using any suitable method for producing a nucleic acid, such as the chemical synthesis and recombinant methods disclosed herein (see, examples section) or such methods known to one of skill in the art. In one embodiment, for example, antisense RNA molecules of the invention may be prepared by de novo chemical synthesis or by cloning. For example, an antisense RNA that hybridizes to L1RT mRNA can be made by inserting (ligating) a sequence set forth in SEQ ID NO:1 in reverse orientation, operably linking it to a promoter and expressing it in an expression vector (e.g., plasmid). Provided that the promoter and, preferably termination and polyadenylation signals, are properly positioned, the strand of the inserted sequence corresponding to the noncoding strand will be transcribed and act as an antisense sequence of the present invention.

In some embodiments, the antisense sequences may also include modified antisense nucleic acid sequences having nucleotide additions, substitutions, deletions or modifications, or other nucleic acid sequences or non-nucleic acid moieties so long as specific binding to the relevant target sequence, i.e., L1RT RNA or its gene/cDNA, is retained as a functional property of the sequences.

For example, a modified antisense nucleic acid sequence consisting of the nucleotides identical to that set forth in SEQ ID NO: 2, 3, 4, 5 or 6 except that, over the entire length corresponding to the nucleotide sequence of SEQ ID NO: 2, 3, 4, 5 or 6, the modified antisense nucleic acid sequence has one or more nucleotide substitutions, deletions or insertions. Identity or similarity, as known in the art, is a relationship between two or more polynucleotide sequences as determined by comparing the sequences. Identity also means the degree of sequence relatedness between polynucleotide sequences, as determined by the match between strings of such sequences from 5' to 3' end for polynucleotides. "Identity" can be readily calculated by art known methods. See e.g., Altschul et al., *Nucleic Acids Res.*, 25:3389-3402 (1997). For example, sequence identity may be optimized by alignment algorithms known in the art and calculating the percent difference between the nucleotide sequences. Effective antisense sequences can be determined by using, for example, GCG (Genetics Computer Group, Madison Wis.) or combinatorial arrays of oligonucleotides or DNA microarrays, which techniques are known to one skilled in the art.

In the present invention, L1RT antisense polynucleotides, RNA, DNA or modified nucleic acid that can be produced by direct chemical synthesis may also be used. Chemical synthesis is generally preferred for the production of oligonucleotides or for oligonucleotides and polynucleotides containing nonstandard nucleotides (e.g., probes, primers and antisense oligonucleotides) for use in the present invention. Direct chemical synthesis of nucleic acids can be carried out by procedures known in the art. One of ordinary skill in the art will recognize that while chemical synthesis of DNA may often be limited to sequences of about 100 or 150 bases, longer sequences may be obtained by the ligation of shorter sequences or by more elaborate synthetic methods. It will be appreciated that the L1RT antisene oligonucleotides of the invention can be made using nonstandard bases or nonstandard backbone structures to provide desirable properties such as, for example, increased nuclease-resistance, tighter-binding, stability or a desired $T_m$).

A wide variety of useful modified oligonucleotides may be produced, including peptide nucleic acid (PNA). Peptide nucleic acid is an analogue of DNA in which the backbone is a pseudopeptide (an amide, in particular N-ethylaminoglycine backbone) rather than a sugar (see, Peter E. Nielsen (Ed), Peptide Nucleic Acids: Protocols and Applications, First Edition, 1999, Horizon Scientific Press). Such a backbone has been reported to result in stronger binding and greater specificity than normally achieved. In addition, the unique chemical, physical and biological properties of PNA have been exploited to produce powerful biomolecular tools, antisense and antigene agents, molecular probes and biosensors. Further teaching of PNA compounds can be found in U.S. Pat. Nos. 5,539,082; 5,714,331 and 5,719,262.

In some embodiments, chimeric oligonucleotides, triplex-forming antisense sequences, RNA-DNA oligonucleotides (RDO), oligonucleotides having backbone analogues, such as phosphodiester, phosphorothioate, phosphorodithioate and such others known in the art may be synthesized and used. For example, a series of antisense phosphorothioate oligonucleotides, 30 nucleotides in length, targeting a nucleic acid encoding L1RT may be used.

It is often useful to label the antisense polynucleotides of the invention, for example, when the L1RT polynucleotides are to be used for detection of L1RT expression, or for the diagnosis and prognosis of conditions related to the inappropriate hyperproliferation. The labels may be incorporated by any of a number of means well known to those of skill in the art. Suitable labels are any composition detectable by photochemical, biochemical, immunochemical, chemical, or spectroscopic means. For example, useful labels include $^{32}P$, $^{35}S$, fluorescent dyes, enzymes (e.g., as commonly used in an ELISA), biotin-streptavadin, digoxigenin, haptens and proteins for which antisera or monoclonal antibodies are available, or nucleic acid molecules with a sequence complementary to a target. The label often generates a measurable signal, such as radioactivity, that can be used to quantitate the amount of bound detectable moiety.

In another aspect of the invention double-stranded RNAs (dsRNAs) corresponding to a defined target region in L1RT mRNA, are used as inhibitors or antagonists of L1RT. The dsRNAs induce RNA-targeted gene-silencing of L1RT which result in reduction or loss of L1RT expression in targeted cells. RNA-targeted gene silencing is well known to one of ordinary skill in the art (Ahlquist, 2002, Science, 296:1270-1273). The dsRNAs may be endogenously synthesized or exogenously applied but only catalytic amounts of dsRNA are required to induce the silencing. A nucleotide sequence from a portion of the L1RT gene is chosen to produce inhibitory RNA, which may be partially or fully double-stranded type. The inhibition is specific because a nucleotide sequence from a portion of the target gene is chosen to produce inhibitory RNA.

There are different methods known in the art to induce RNA-targeted gene-silencing such as small interfering RNA, short hairpin RNA, expressed long interfering RNA, expressed short interfering RNA and expressed short hairpin RNA. It is preferred that certain dsRNAs (small interfering RNA and short hairpin RNA) include modifications to either the phosphate-sugar backbone or the nucleoside. The RNA duplex formation may be initiated either inside or outside the cell. The RNA may be introduced in an amount which allows delivery of at least one copy per cell with higher doses of double-stranded material may yield more effective inhibition. Inhibition is sequence-specific in that L1RT mRNA nucleotide sequences corresponding to the duplex region of the RNA are targeted for genetic inhibition. RNA sequences with insertions, deletions, and single point mutations relative to the target sequence can also be found to be effective for inhibition.

The RNA may be delivered to cells or directly introduced into intercellular spaces of a tissue or into the vascular system of an organism. It may also be delivered orally to the patients. Methods for oral introduction include direct mixing of dsRNA with food of the patient, as well as engineered approaches in which a species that is used as food is engineered to express the RNA, then fed to the organism to be affected. Physical methods of introducing nucleic acids include injection directly into the cell or extracellular injection into the patient of an RNA solution.

In another aspect, dominant negative mutants of the L1RT protein or nucleic acids having a sequence encoding a dominant negative mutant L1RT protein or non-functional fragment or derivative thereof are administered to inhibit L1RT function by interfering with the interactions of L1RT and with other molecules in the cell. It is believed that the L1RT must directly interact with a portion of the telomere for telomere eleongation.

Therefore, L1RT mutants that are defective in function but effective in binding to the portion of the telomere can be used as a dominant negative mutant to compete with the wild type L1RT. Dominant non-functional L1RT can be engineered for expression in cancer cells that inappropriately overexpress L1RT. Given that the protein and nucleic acid sequences of the wild type L1RT is known, one skilled in the art can create dominant negative mutants of L1RT suitable for use in the present invention. Such dominant negative mutants may be administered to cells in vivo or in vitro according to the standard delivery methods already known in the art. In a preferred aspect of the invention, the therapeutic nucleic acid has an L1RT nucleic acid that is part of an expression vector that expresses a dominant non-functional L1RT protein or fragment or chimeric protein thereof in cancer cells.

In another aspect of the present invention, antibodies or binding portions thereof specific to L1RT are used as inhibitors or antagonists of L1RT. Specifically, the present invention contemplates the prevention and treatment of L1RT induced cancer in humans as well as other animals through the use of antibodies to L1RT. Both polyclonal and monoclonal antibodies and binding portions (Fab fragments and Fv fragments) of such antibodies are contemplated in the context of the present invention. Such antibodies may be made in a variety of animals including, mice, rabbits, monkeys, chimpanzees, cows (e.g., in the milk) and birds. The present invention also contemplates human and humanized antibodies. The antibodies can be used preventively or during the acute stage of pathological cell proliferation.

In one embodiment, the present invention contemplates a method in which the antibodies which bind to L1RT protein are administered so that the antibodies react with L1RT. In another embodiment, the antibodies are combined with other reagents including but not limited to other antibodies. The administration of antibodies can be carried out orally, parenterally or by other suitable routes.

The antibody production may be effected by techniques which are well-known in the art. For example, mammalian lymphocytes are immunized by in vivo immunization of the animal (e.g., a mouse) with human L1RT protein or polypeptide. Such immunizations are repeated as necessary at intervals of up to several weeks to obtain a sufficient titer of antibodies. Hybridomas may be produced and cultured, and the resulting colonies are screened for the production of the desired monoclonal antibodies. Colonies producing such antibodies are cloned, and grown either in vivo or in vitro to produce large quantities of antibody.

The dose of a given inhibitor or antagonist of L1RT can be determined by one of ordinary skill in the art upon conducting routine experiments. Prior to administration to patients, the efficacy may be shown in experimental animal models. In this regard any animal model for L1RT induced cancer known in the art can be used (Hahn et al., 1999, Nature Medicine, 5(10):1164-1170; Yeager et al., 1999, Cancer Research, 59(17): 4175-4179). For example, immunodeficient mice (Balb/c-ByJ-Hfh1 1nu; Jackson Laboratory) are obtained and maintained in pathogen-free conditions prior to xenograft tumor induction. To create human ALT cell line that will be tumorigenic in mice the IIICF/c fibroblast cell line (showing ALT) is transfected with pSV2neo-EJras plasmid (containing the activated c-Ha-ras oncogene from the EJ bladder carcinoma cell line) DNA, and selected with G418.

Xenograft tumors can be subcutaneously generated in immunodeficient mice by the injection of the transformed IIICF/c fibroblast cells. About $2 \times 10^6$ cells may be injected subcutaneously into the mice, preferably along their dorsal flanks, anaesthetized with Metofane. The growing tumours may be measured every 2-3 days. Tumor growth was followed by measuring with a caliper the longest axis of the tumor and the axis perpendicular to this. Tumor volume may be calculated using the formula $4/3\pi r^3$, where r is the radius of the tumor. The tumors may be excised and weighed prior to processing. Tissues to be used for molecular biological analysis may be snap frozen in liquid nitrogen and stored at −80.degree. C. The xenograft tumors will have no detectable telomerase activity in the Telomeric Repeat Amplification Protocol (TRAP) assay. The TRF length pattern diagnostic of cells showing ALT may be verified by Southern analysis.

After induction of tumors, mice in the experimental groups may be treated with AZT. Mice may be injected i.p. twice a day with solution of AZT in PBS with a total daily dose of 10 mg/kg. Mice in control group may be injected with PBS. Alternatively, AZT at the same daily dose may be given in drinking water. Mice in the control group will bear the actively growing tumors and none of the mice in experimental groups will have tumors. As a separate set of controls, telomerase-positive tumors in nude mouse may be induced by injecting the immunodeficient mice with WM1175 (malignant melanoma) or HUT292DM (lung cancer) cells instead of the transformed IIICF/c fibroblast cells. The telomerase-positive tumors in the immunodeficient mice cannot be inhibited by the AZT at the dose tested.

Thus, the efficacy of various inhibitors or antagonists may be shown in standard experimental animal models prior to administration to subjects or patients. The subject, or patient, to be treated using the methods of the invention is preferably human, and can be a fetus, child, or adult. Other an animal mammals that may be treated can be mice, rats, rabbits, monkeys and pigs.

The inhibitors or antagonists can be used alone or in combination with other chemotherapeutics or otherwise. For example, therapy of L1RT induced cancers may be combined with chemo and/or radiotherapy to treat cancers induced by telomerase or some other factors. Examples of chemotherapeutic agents known to one skilled in the art include, but are not limited to, anticancer drugs such as bleomycin, mitomycin, nitrogen mustard, chlorambucil, 5-fluorouracil (5-FU), floxuridine (5-FUdR), methotrexate (MTX), colchicine and diethylstilbestrol (DES). To practice combined therapy, one would simply administer to an animal an inhibitor component of the present invention in combination with another anticancer agent in a manner effective to result in their combined anti-cancer actions within the animal or patient. The agents would therefore be provided in amounts effective and for periods of time effective to result in their combined presence in the region of target cells. To achieve this goal, the agents may be administered simultaneously, either in a single composition, or as two distinct compositions using different administration routes. Alternatively, the two treatments may precede, or follow, each other by, e.g., intervals ranging from minutes to hours or days. By way of example, and not limitation, doses of AZT for systemic use may be 500 mg/kg per day for human adults, 20 mg/kg per day for mice and human infants.

Some variation in dosage may occur depending on the condition of the subject being treated. The physician responsible for administration will be able to determine the appropriate dose for the individual patient and may depend on multiple factors, such as, the age, condition, file history, etc., of the patient in question.

Accordingly, the methods of the invention can be used in therapeutic applications for conditions and diseases associated with L1RT induced pathological proliferation of cells. Diseases that would benefit from the therapeutic applications of this invention include all diseases characterized by cell hyperproliferation including, for example, solid tumors and leukemias, and non-cancer conditions. It is further contemplated that the method of the invention can be used to inhibit the growth of cancer cells not only in an in vivo context but also in an ex vivo situation. The method of the invention is particularly useful for inhibiting the growth of pathologically proliferating human cells ex vivo, including, but not limited to, human cancer cells—osteosarcoma, breast carcinoma, ovarian carcinoma, lung carcinoma, adrenocortical carcinoma or melanoma.

The present invention provides methods and kits for identifying inappropriately, pathologically or abnormally proliferating cells due to the expression of L1RT in the cells. The methods can be used as a screening method that aids in diagnosing the presence of a cancerous cell or tumor in a patient by determining the presence (and/or level) of expression of L1RT in tissue from the patient, the presence of L1RT expression being indicative of cancer cells or pathological cell proliferation in the patient.

For example, cancerous tumor samples can be diagnosed by the detection of L1 specific mRNA expression measured by a variety of methods including, but not limited to, hybridization using nucleic acid, Northern blotting, in situ hybridization or RNA microarrays, or the presence of L1 retrotransposon ORF1 and/or ORF2 encoded proteins measured by variety of methods including, but not limited to, Western blotting, immunoprecipitation or immunohistochemistry, or enzymatic activity of reverse transcriptase.

Cancer cells showing ALT can also be diagnosed by determining the absence of catalytic subunit mRNA expression (measured by a variety of methods including, but not limited to, Northern blotting, RNA protection assay, in situ hybridization, RT-PCR, real time RT-PCR or RNA microarrays), or the absence of telomerase catalytic subunit translation (measured by a variety of methods including, but not limited to, Western blotting, immunoprecipitation or immunohistochemistry). Another characteristic of cells showing ALT is the presence of long and heterogeneous telomeres (Bryan et al., 1997, Nature Medicine, 3:1271-1274). Accordingly, a diagnostic method may include detection of the presence of long and heterogeneous telomeres as an indicator of cells with ALT. The method includes, but is not limited to, terminal restriction digest and its modification, in situ hybridization with a telomere specific probe or flow cytometry with telomere specific DNA or PNA probes.

In a preferred embodiment, nucleic acid probes directed against L1RT can be used to detect presence and/or increases in L1RT mRNA levels in tissues undergoing rapid proliferation, such as primary cancer cells, including human osteosarcoma, breast carcinoma, ovarian carcinoma, lung carcinoma, adrenocortical carcinoma or melanoma. Thus, the present invention provides methods of using nucleic acid probes that are complementary to a subsequence of an L1RT to detect and identify pathologically proliferating cells, including cancer cells. For example, the method for identifying a pathologically proliferating cell may involve using a nucleic acid probe directed against an L1RT mRNA to compare the level of expression of L1RT mRNA in a test cell with the level of expression of L1RT mRNA in a control cell. A test cell is identified as a pathologically proliferating cell when the level of L1RT expression is observed as in the control cell.

It is preferred that the nucleic acid probe used in the method of the present invention is fully complementary to a human L1RT nucleic acid sequence, preferably mRNA, and the test cell is a human cell. An example of nucleic acid probe that is fully complementary to a human L1RT RNA sequence is 5'-TCC TGC TTT CTC TTG TAG GCA-3' (SEQ ID NO:6). The nucleic acid probe used in the method of the invention, however, may also be substantially complementary to an L1RT mRNA or an L1RT retrotransposon RT sequence of human mouse or other mammal. It will be apparent to one of ordinary skill in the art that substitutions may be made in the nucleic acid probe which will not affect the ability of the probe to effectively detect the L1RT RNA in pathologically proliferating cells (e.g., cancer cells) and thus, such substitutions are within the scope of the present invention. The nucleic acid probe used in the method of the present invention can be a DNA probe, or a modified probe such a peptide nucleic acid probe, a phosphorothioate probe, or a 2'-O methyl probe. The length of the nucleic acid probe may be from about 8 or 10 to 50 nucleotides, preferably from about 15 to 25 nucleotides in length. The method of the invention can be readily performed in a cell extract, cultured cell, or tissue sample from a human, a mammal, or other vertebrate.

The methods of the present invention are useful for detecting the inappropriately, pathologically or abnormally proliferating cells due to the expression of L1RT in the cells in vitro, in cell cultures, and in human cells and tissues, such as solid tumors and cancers (e.g., human osteosarcoma, breast carcinoma, ovarian carcinoma, lung carcinoma, adrenocortical carcinoma or melanoma).

The present invention also provides kits for detecting and/or inhibiting hyperproliferating cells or cancer cells. The kit can have a nucleic acid probe that is fully or substantially complementary to a subsequence of an L1RT mRNA. The kits for inhibiting the proliferation of pathologically proliferating cells, the kit comprising the step of contacting the cells with may have an agent, e.g., an antisense oligonucleotide that is substantially complementary, preferably fully complementary, to a subsequence of an L1RT nucleic acid, which agent upon contacting the cells can affect pathological proliferation. The kits can be in the form of a container containing one or more of the above-discussed nucleic acid probes, antisense oligonucleotides, or other suitable agents with or without detection labels discussed herein. The kits may contain a suitable membrane for separation and hybridization of sample RNA, DNA or protein, preferably in the form of an assay apparatus that is adapted to use with the claimed methods. The kits can also include instruction manuals for carrying out the methods of the present invention. The kits may also include reagents useful for detecting the presence of the detectable labels and/or materials useful in the performance of various assays including positive, negative controls, internal and/or external controls. Exemplary reagents and materials are RNA extraction buffers, hybridization buffers, test tubes, transfer pipettes, and the like.

The inhibitors or antagonists of the L1RT that can be used in methods of the present invention should not be limited in any way to the specific compounds mentioned in the present application. Given that the present invention discloses a target responsible for hyperproliferation of cells, a number of other useful inhibitors or antagonists of the L1RT can be identified by simple screening methods. The active compounds may include fragments or parts of naturally-occurring or prior art compounds. However, prior to testing of such compounds in humans, it may be necessary to test a variety of candidate agents in screening assays to determine which have potential as anti-tumor drugs. A number of assays are known in the art for determining the effect of a drug on cancer. Therefore, in particular embodiments, the present invention concerns a method for identifying or selecting compounds that will modulate expression or activity of L1RT. Drugs which interfere with the biological activity of L1RT are good candidates for anti-tumor drugs, because they affect one of the steps that leads to uncontrolled proliferation or a continuous increase in cell number.

Screening for compounds or drugs may be performed using purified L1RT enzyme, an in vitro model, cell cultures, a genetically altered cell or animal, or xenograft model antitumor assays. Of particular interest are screening assays for agents that have a low toxicity for human cells. Candidate agents encompass numerous chemical classes, though typically they are organic molecules, antisense polynucleic acids or small organic compounds having a molecular weight of more than 50 and less than about 2,500 daltons, analogs of purines and pyrimidines or combinations thereof. Known pharmacological antitumor agents may be subjected to further chemical modifications, such as amidification, to produce structural analogs. If the screening assay is a binding assay, one or more of the molecules may be joined to a label, where the label can directly or indirectly provide a detectable signal. Various labels such as radioisotopes, fluorochromes, chemiluminescent agents, enzymes and specific binding molecules, particles, e.g. magnetic particles may be used. A variety other reagents like salts, neutral proteins, e.g. albumin, detergents, etc may also be used to facilitate optimal proteinprotein binding and/or reduce non-specific or background interactions. Reagents that improve the efficiency of the assay, such as protease inhibitors, nuclease inhibitors, antimicrobial agents may be used.

For example, a screening assay or a method for identifying a compound or agent in its simplest form may include incubating a candidate compound or compounds to be tested with a cell expressing L1RT under conditions in which, but for the presence of the compound or compounds to be tested, the interaction of L1RT and other cell components induces a detectable or measurable biological effect or a chemical effect (example addition of nucleotides or analogs to the telomere or maintenance of telomere length) and then determining the ability of L1RT to interact with the cell components to induce the detectable or measurable biological effect or the chemical effect in the presence of the compound or compounds to be tested. If the candidate compound or the tested compound modulates the interaction L1RT with other cell components, then that compound is selected.

Other assays of interest can be, for example, a cell line expressing L1RT or an expression construct having an L1 RT gene may be introduced into a cell line under conditions that allow L1RT expression. To this cell line candidate agent(s) is(are) added, and the ability to inhibit or down-regulate L1RT activity is detected. The level of L1RT activity may be determined by a functional readout or assay including alterations in L1RT expression levels, binding or inhibition of binding to a telomere or some other substrate, apoptosis, presence or lack of growth, presence or lack of metastasis, presence or lack of cell division, presence or lack of cell migration, presence or lack of soft agar colony formation, presence or lack of contact inhibition, presence or lack of invasiveness, and/or presence or lack of tumor progression or other malignant phenotype.

For example, a method for determining the ability of a candidate compound to decrease the wild-type L1RT expression in cells and to concomitantly induce apoptosis in those cells may be carried out by obtaining a cell expressing L1RT, admixing a candidate substance with the cell; and determining the ability of the candidate substance to reduce the L1RT content and/or telomere length on the chromosomes of the cell.

Another simple example to identify a candidate substance as being capable of interfering with L1RT expression can be as follows: one may measure or determine the L1RT status of a cell. If that cell has the ability to express L1RT, its basal L1RT content in the absence of the added candidate compound is measured. One may then add the candidate compound to the cell and re-determine the wild-type L1RT expression in the presence of the candidate compound. A candidate compound that decreases the L1RT expression relative to the cell's L1RT expression in the absence of the test or candidate compound is indicative of a candidate compound with wild-type L1RT expression inhibiting capability. It can, therefore, have prophylactic and therapeutic cancer reducing and apoptotic potential.

The present invention also encompasses the use of various animal models. By developing or isolating cell lines that express L1RT one can generate disease models in various laboratory animals. These models may employ the subcutaneous, orthotopic or systemic administration of cells to mimic various disease states. For example, the IIICF/c fibroblast cell line (ALT) can be transfected with pSV2neo-EJras plasmid DNA (containing the activated c-Ha-ras oncogene from the EJ bladder carcinoma cell line), selected with G418, and injected subcutaneously into nude mice to obtain ALT tumors. The resulting tumors do not show any detectable telomerase activity in telomeric repeat amplification protocol (TRAP) assay, and Southern analysis shows that they retained the TRF length pattern diagnostic of ALT (Yeager et al., Cancer Res. 1999, 59(17):4175-9). Finally, telomerase knock out animals (e.g., telomerase KO mice −/−; Rudolph et al., 1999, Cell, 96:701-712) or transgenic animals that express a wild-type L1RT as a transgene in the animals may be utilized as models for treatment. Of course, animal models provide a useful vehicle for testing combinations of agents as well. Determining the effectiveness of a compound in vivo may involve a variety of different criteria including, but are not limited to, survival, tumor regression, arrest or slowing of tumor progression, elimination of tumors and inhibition or prevention of metastasis.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Of course, the screen may include appropriate control values (e.g., the level of L1RT expression or production in isolated cells or animals showing ALT in the absence of candidate compound(s)). Test compounds or candidate compounds which are considered positive, i.e., likely to be beneficial in the treatment of cancer will be those which have a substantial growth inhibitory effects (e.g., test agents that are able to reduce the growth of cells preferably by at least 20% more preferably by at least 50%, and most preferably by at least 80%, still more preferably by about 90 to 100%.

Such compounds would be important in a number of aspects. They would be important in regimens for the treatment of L1RT-related cancers, whether administered alone or in combination with chemo- and radiotherapeutic regimens known to one skilled in the art in the treatment of cancer. Alternatively, by simply reducing L1RT, these compounds will be instrumental in selectively inducing massive apoptosis of cancer cells.

The compounds having the desired pharmacological activity are selected and may be administered in a physiologically or pharmaceutically acceptable carrier to a host for treatment of proliferative diseases, etc. Pharmaceutically acceptable carriers are determined in part by the particular composition being administered (e.g., nucleic acid, protein, organic compound, a vector or transduced cell), as well as by the particular method used to administer the composition. Accordingly, there are a wide variety of suitable formulations of pharmaceutical compositions of the present invention.

A pharmaceutical composition in the present invention may contain recombinant products. For example, the antisense oligonucleotides or dsRNA targeted to L1RT can be inserted into any of a number of well-known vectors for the transfection of target cells and organisms. For example, nucleic acids are delivered as DNA plasmids, naked nucleic acid, and nucleic acid complexed with a delivery vehicle such as a liposome. Viral vector delivery systems include DNA and RNA viruses (Porter, 2004, Retroviral vectors for suicide gene therapy, Methods Mol Med., 90:91-106; Wang et al., 2004, Prolonged and inducible transgene expression in the liver using gutless adenovirus: A potential therapy for liver cancer, Gastroenterology, 126:278-289). In a specific embodiment, a viral vector that contains an antisense L1RT nucleic acid is used. For example, a retroviral vector or adenoviral vector known in the art for cancer gene therapy can be used. The antisense L1RT nucleic acid to be used in gene therapy is cloned into a suitable vector, which facilitates delivery of the gene into a patient.

Methods of non-viral delivery of nucleic acids may include naked polynucleotide, agent-enhanced uptake of polynucleotide, microinjection, particle bombardment, liposomes, immunoliposomes, polycation or lipid:nucleic acid conjugates. Delivery can be to cells (ex vivo administration) or target tissues (in vivo administration) (Narayanan, Antisense therapy of cancer, In Vivo. 1994, 8(5):787-793; Zhang et al., Anti-oncogene and tumor suppressor gene therapy—examples from a lung cancer animal model, In Vivo. 1994, 8(5):755-769. In a particular embodiment, a nucleic acid molecule is used in which the antisense L1RT sequences and any other desired sequences are flanked by regions that promote homologous recombination at a desired site in the genome, thus providing for intrachromosomal expression of the antisense L1RT nucleic acid. An example of the sequences that flank 5' end of L1RT ORF (ORF2) 5'-agaccat caagactagg aagaaactgc atcaactaat gagcaaaatc accagctaac atcata-3' (SEQ ID NO:7).

The inhibitory or antagonistic agents may be administered in a variety of ways including orally, topically, parenterally e.g. subcutaneously, intraperitoneally, by viral infection, intravascularly, etc. Depending upon the manner of introduction, the compounds may be formulated in a variety of ways. Formulations suitable for oral administration can be liquid solutions. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions. In the practice of this invention, compositions can be administered, for example, by intravenous infusion, orally, topically, parenterally or intraperitoneally. Oral and parenteral administrations are the preferred methods of administration.

The dose administered to a patient, in the context of the present invention, should be sufficient to effect a beneficial therapeutic response in the patient over time. The dose will be determined by the efficacy of the particular inhibitor or antagonistic agent employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

For administration, compounds of the present invention can be administered at a rate determined by the LD-50 of the compound, and the side-effects of the compound at various concentrations, as applied to the mass and overall health of the patient. Administration can be accomplished via single or divided doses or, e.g., by administration to the site of a solid tumor in a slow release formulations.

EXAMPLES

The following examples further illustrate the present invention. The examples below are carried out using standard techniques, that are well known and routine to those of skill in the art, except where otherwise described in detail. The examples are offered by way of illustration and not by way of limitation.

Example 1

Induction of Telomere Shortening, G2 Arrest and Apoptosis in Telomerase Negative ALT Cells after AZT Treatment To detect L1 specific RNA in two cell lines (U-2 OS and Saos-2 osteosarcomas), reported to maintain telomeres by ALT mechanism[4], total mRNA was analyzed by dot blotting with an L1 retrotransposon specific probe. The reported telomerase-positive cell lines (HEC-1 and HeLa) were used for comparison[4,21] (FIG. 1). Both ALT cell lines were positive in this test. HEC-1 cells were completely negative, with only traces of L1 transcripts in HeLa cells, as previously reported[20].

Figure 2:
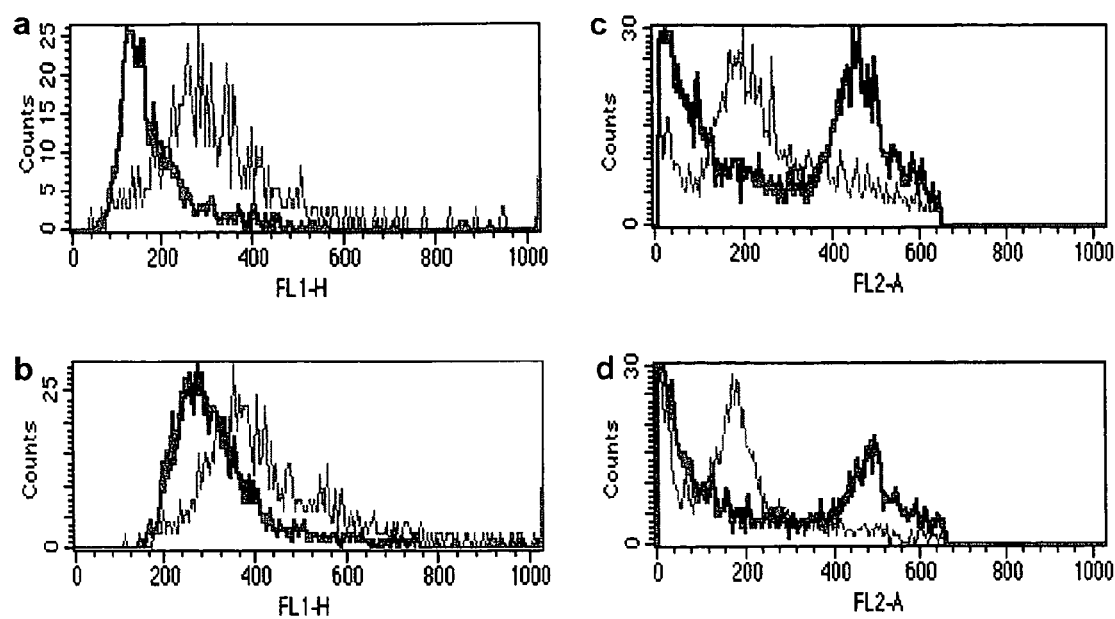
FIG. 2 illustrates flow cytometry data showing decrease in telomere length, massive apoptosis and changes in cell cycle after 14 days of treatment of ALT cell lines with AZT. Telomere specific fluorescence in G2 phase of cell cycle. (a) Saos-2; (b) U-2 OS. Cell cycle distribution[22] (c) Saos-2; (d) U-2 OS. Untreated cells—dark, treated—grey.

Further to test the proposed method, ALT cell lines were treated with therapeutic concentrations of AZT, to determine if slippage telomeric DNA synthesis could be inhibited by AZT-TP, and thereby induce telomere shortening. Telomere length in AZT treated and untreated cell lines was measured by flow cytometry with a telomere-specific peptide nucleic acid (PNA) probe[22,23]. To determine cell cycle distribution, cells were stained with propidium iodide (PI)[22]. After 14 days of AZT treatment, both ALT cell lines demonstrated telomere shortening, massive apoptosis and G2 arrest (FIG. 2). To confirm the specificity of AZT-induced telomere shortening for ALT cells, a HeLa cell line, known to be positive for telomerase, was treated with AZT under the same conditions. AZT at the chosen concentration had no effect on telomere length or cell cycle distribution in the HeLa cells (not shown).

Figure 3:
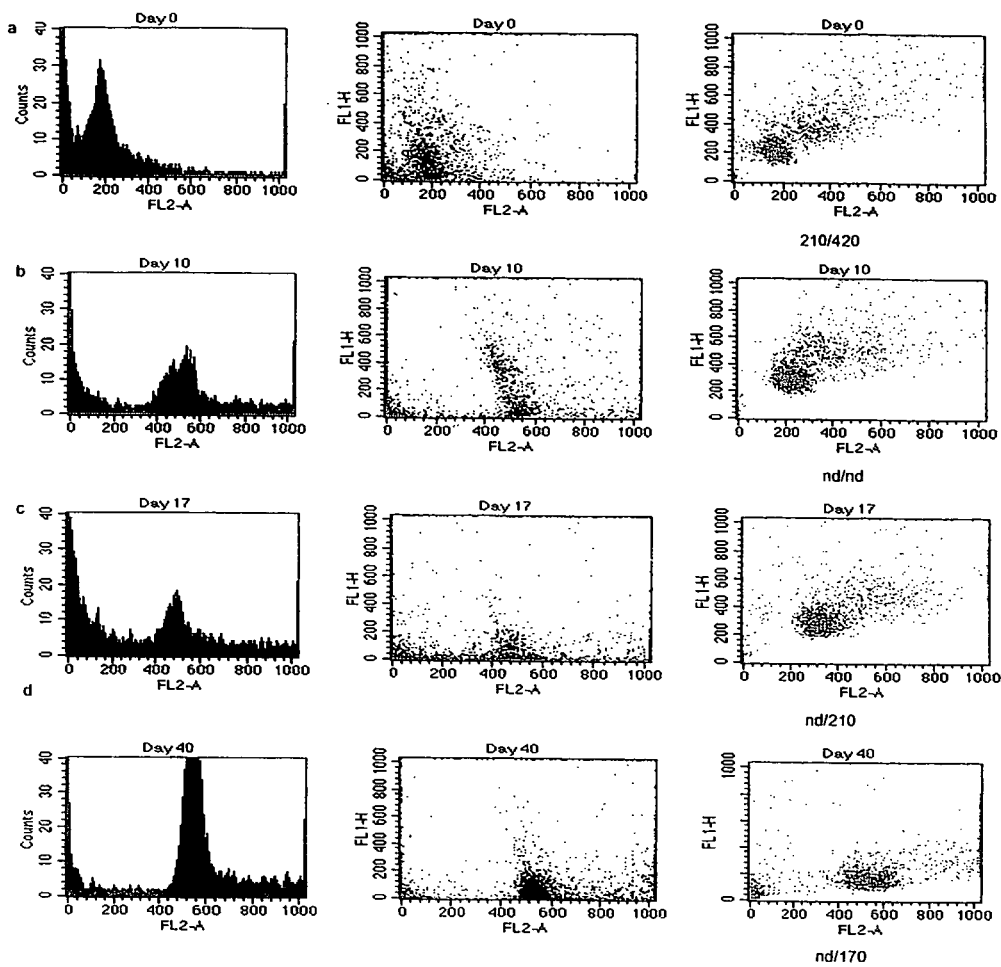
FIG. 3 illustrates flow cytometry data showing changes in DNA synthesis rate, cell cycle distribution and telomere length in U-2 OS cells treated with AZT for different amounts of time. a, b, c, d no treatment and treatment for 10, 17, and 40 days respectively. Cell cycle distribution[24]—left. Staining for BdU incorporation (FITC) and PI[24]—middle. Staining with PNA-FITC and PI—right. The numbers indicate telomere specific fluorescence measured in arbitrary units[22] in G1 and G2 phases respectively.

To demonstrate telomere shortening and changes in DNA synthesis rate, dynamic, U-2 OS cells were treated with AZT for different amounts of time, and analyzed by flow cytometry simultaneously. Rate of DNA synthesis was determined by incorporation of 5-bromodeoxyuridine (BdU)[24]. Results (FIG. 3) show progressive telomere shortening and decrease in DNA synthesis. It is important to note that changes in cell cycle distribution, DNA synthesis and telomere length were rapid and could be detected after only 10 days of AZT treatment.

At the same time, PI staining demonstrated a higher DNA content in AZT treated cells at later stages of treatment, compared to untreated cells. A rational explanation of this fact is a short telomere induced chromosome end-to-end joining[12,26]. Induction of apoptosis in AZT treated ALT cells seems to be p53 independent since U-2 OS and Saos-2 represent both p53+/+ and p53−/− cancer cell lines[27].

Tumors with suppressed elongation of telomeres have been reported to lose their tumorigenic potential[12,26], and AZT is already in clinical use for treating AIDS. The present disclosure provides that AZT can be used for the treatment of up to 30% of cancer cases. Some other nucleoside reverse transcriptase inhibitors (e.g. 2',3'-dideoxyinosine (ddI) or 2',3'-didehydro-3'-deoxythymidine(d4T)) that are already in clinical practice could also be used.

Example 2

Induction of Telomere Shortening, G2 Arrest and Apoptosis in Telomerase Negative ALT Cells after Antisense Inhibition of L1 Reverse Transcriptase To confirm that ALT is conducted by L1 reverse transcriptase only, U-2 OS cells were transfected expressing constructs containing part of human L1 ORF2 in sense and antisense orientation. The L1 specific reverse transcriptase targeted antisense construct was created as follows: PCR was performed using RT-F (5'-ATG ACA GGA TCA ACT TCA CAC-3') (SEQ ID NO:8), RT-R (5'-TCC TGC TTT CTC TTG TAG GCA-3') (SEQ ID NO:6) primers and pBS-L1$_{RP}$-EGFP plasmid as a template. 929 bp PCR product was cloned in pTargetT vector (Promega).

Figure 4:
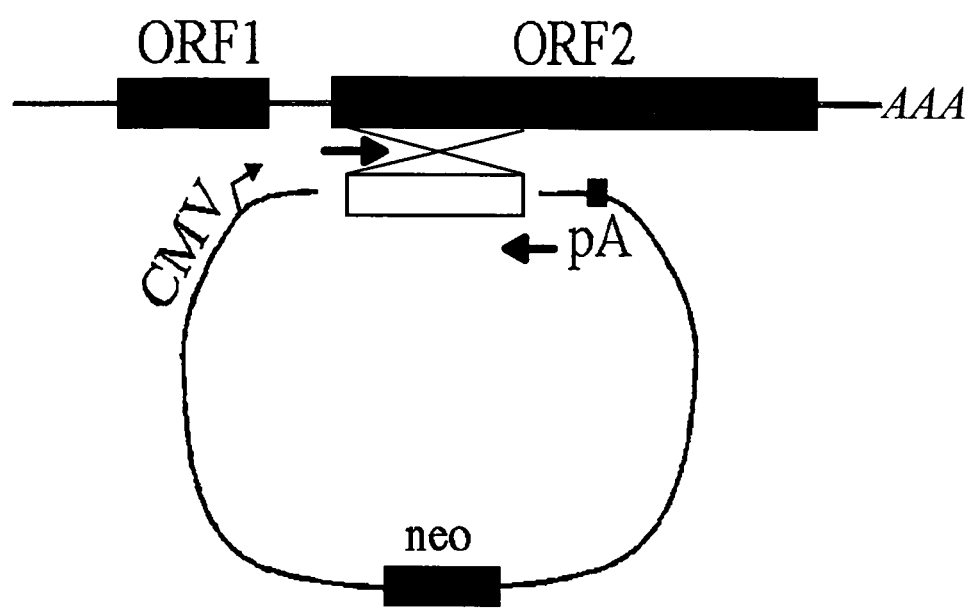
FIG. 4 shows a schematic representation of L1 reverse transcriptase antisense targeting strategy.

Recombinant constructs containing insert in sense and antisense orientation were purified with Plasmid Midi Kit (Qaigen), digested with Xmn I (Promega) and transfected into U-2 OS cells using "Lipofectamine" (Gibco) according to the manufacturers instructions. After 40 days of selection on media containing 0.5 mg/ml of G418 (Gibco), cells were harvested, stained with PNA and PI, and analyzed by flow cytometry[22]. A schematic representation of L1 reverse transcriptase antisense targeting is shown in FIG. 4.

Figure 5:
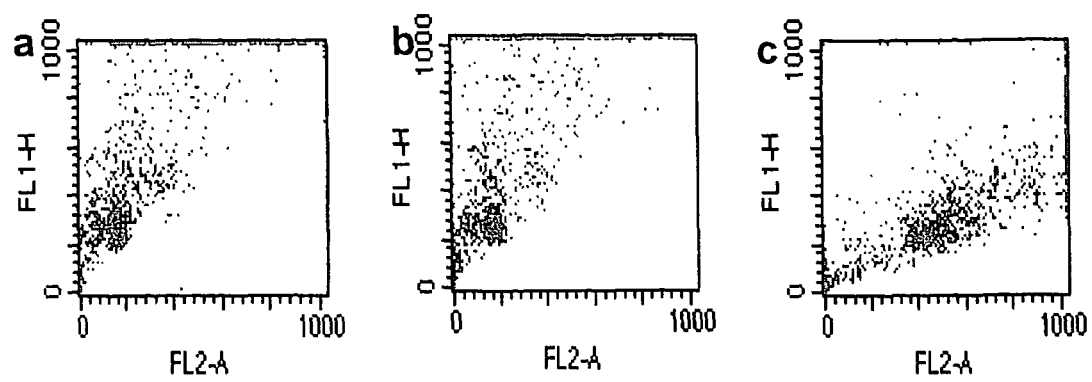
FIG. 5 illustrates flow cytometry data showing changes in cell cycle distribution and telomere length in U-2 OS cells transfected with L1 targeted antisense construct. (a) no treatment; (b) sense construct; (c) antisense construct.

Data presented in FIG. 5 show that cells carrying antisense construct demonstrated massive apoptosis, G2 arrest, and telomere shortening as expected. In contrast, cells expressing sense construct showed no difference in telomere length or cell cycle.

The following materials and procedures were used in the above working examples:

Cell lines: All cell lines used in this study were obtained from American Type Culture Collection (Rockville, Md.). The cells origins included osteosarcoma (Saos-2 and U-2 OS), liver (HEC-1) and uterine cervix (HeLa). Cells were cultured following ATCC recommendation. For treatment of the cells with AZT, the media was supplemented with 0.2 μM of 3'-azido-2',3'-dideoxythymidine (Sigma)[28].

Dot blotting: Total cellular RNA was isolated using "RNA-STA 60" solution (Tel-Test, Inc.). The reaction was performed using 30 μg of total RNA and "HRP North2South" (Pierce) labeled pBS-L1$_{RP}$-EGFP plasmid[29] as a specific probe, according to the manufacturers protocol.

Bromodeoxyuridine incorporation: Cell staining, for BdU incorporation, was performed using cells which were incubated with 10 mM BrdU (Sigma) for 2.5 h, stained with BU-33 anti-BrdU monoclonal antibodies (Sigma) and FITC labeled Alexa 488 goat anti-mouse IgG (H+L) (Fab') fragments (Molecular Probes), contrastained with 50 μg/ml PI (Sigma) and analyzed by flow cytometry as described[24].

Telomere length measurement by flow cytometry: Cell were stained with telomere specific FITC conjugated $(C_3TA_2)_3$ PNA (Applied Biosystems) probe and contrastained with 0.06 μg/ml PI as described[21].

Inhibition of L1 reverse transcriptase using antisense strategy: To create L1 specific reverse transcriptase targeted antisense construct PCR was performed using RT-F(5'-ATG ACA GGA TCA ACT TCA CAC-3') (SEQ ID NO:8), RT-R (5'-TCC TGC TTT CTC TTG TAG GCA-3') (SEQ ID NO:6) primers and pBS-L1$_{RP}$-EGFP plasmid as a template. 929 bp PCR product was cloned in pTargetT vector (Promega). Recombinant constructs containing insert in sense and antisense orientation were purified with Plasmid Midi Kit (Qaigen), digested with Xmn I (Promega) and transfected into U-2 OS cells using "Lipofectamine" (Gibco) according to the manufacturers instructions. After 40 days of selection on media containing 0.5 mg/ml of G418 (Gibco), cells were harvested, stained with PNA and PI, and analyzed by flow cytometry[22].

The references numbered 1-29 below are cited in the above description (with the corresponding superscript numbers) and as such one skilled in the art would match the references to the appropriate superscript numbers in the text above.

1. Greider, C. W., Blackburn, E. H. Identification of a specific telomere terminal transferase activity in Tetrahymena extracts. *Cell* 43, 405-413 (1985).
2. Wright, W. E., Piatyszek, M. A., Rainey, W. E., Byrd, W., Shay, J. W. Telomerase activity in human germline and embryonic tissues and cells. *Dev. Genet.* 18, 173-179 (1996).
3. Kim, N. W., Piatyszek, M. A., Prowse, K. R., Harley, C. B., West, M. D. Specific association of human telomerase activity with immortal cells and cancer. *Science* 266, 2011-2015 (1994).
4. Bryan, T. M., Englezou, A., Dalla-Pozza, L., Dunham, M. A., Reddel, R. R. Evidence for an alternative mechanism for maintaining telomere length in human tumors and tumor-derived cell lines. *Nat. Med.* 3, 1271-1274 (1997).
5. Reddel, R. R., Bryan, T. M., Colgin, L. M., Perrem, K. T., Yeager, T. R. Alternative lengthening of telomeres in human cells. *Radiat. Res.* 155, 194-200 (2001).
6. Kazazian, H. H. Jr, Moran, J. V. The impact of L1 retrotransposons on the human genome. *Nat. Genet.* 19, 19-24 (1998).
7. Nozawa, K., Suzuki, M., Takemura, M., Yoshida, S. In vitro expansion of mammalian telomere repeats by DNA polymerase alpha-primase. Nucleic Acids Res. 28, 3117-3124 (2000).
08. Olovnikov, A. M. Principle of marginotomy in template synthesis of polynucleotides. *Dokl. Akad. Nauk SSSR* 201, 1496-1499 (1971).
9. Allshire, R. C., Dempster, M., Hastie, N. D. Human telomeres contain at least three types of G-rich repeat distributed non-randomly. *Nucleic Acids Res.* 17, 4611-4627 (1989).
10. Harley, C. B., Futcher, A. B., Greider, C. W. Telomeres shorten during ageing of human fibroblasts. *Nature* 34, 458-460 (1990).
11. Hahn, W. C. et al. Inhibition of telomerase limits the growth of human cancer cells. *Nat. Med.* 5, 1164-1170 (1999).
12. Bryan, T. M. and Reddel, R. R. Telomere dynamics and telomerase activity in in vitro immortalised human cells. *Eur. J. Cancer* 33, 767-773 (1997).
13. Bryan, T. M., Englezou, A., Gupta, J., Bacchetti, S., Reddel, R. R. Telomere elongation in immortal human cells without detectable telomerase activity. *EMBO J.* 14, 4240-4248 (1995).

14. Gupta, J., Han, L. P., Wang, P., Gallie, B. L., Bacchetti, S. Development of retinoblastoma in the absence of telomerase activity. *J. Natl. Cancer Inst.* 88, 1152-1157 (1996).
15. Dunham, M. A., Neumann, A. A., Fasching, C. L., Reddel, R. R. Telomere maintenance by recombination in human cells. *Nat. Genet.* 26, 447-450 (2000).
16. Mathias, S. L., Scott, A. F., Kazazian, H. H. Jr, Boeke, J. D., Gabriel, A. Reverse transcriptase encoded by a human transposable element. *Science* 254, 1808-1810 (1991).
17. Clements, A. P., Singer, M. F. The human LINE-1 reverse transcriptase: effect of deletions outside the common reverse transcriptase domain. *Nucleic Acids Res.* 26, 3528-3535 (1998).
18. Skowronski, J., Singer, M. F. Expression of a cytoplasmic LINE-1 transcript is regulated in a human teratocarcinoma cell line. *Proc. Natl. Acad. Sci. USA* 82, 6050-6054 (1985).
19. Bratthauer, G. L., Fanning, T. G. Active LINE-1 retrotransposons in human testicular cancer. *Oncogene* 7, 507-510 (1992).
20. Moran, J. V et al. High frequency retrotransposition in cultured mammalian cells. *Cell* 87, 917-927 (1996).
21. Murakami, J., Nagai. N., Shigemasa. K., Ohama. K. Inhibition of telomerase activity and cell proliferation by a reverse transcriptase inhibitor in gynaecological cancer cell lines. *Eur. J. Cancer* 35, 1027-1034 (1999).
22. Rufer, N., Dragowska, W., Thornbury G., Roosnek, E., Lansdorp P. M. Telomere length dynamics in human lymphocyte subpopulations measured by flow cytometry. *Nat. Biotechnol.* 16, 743-747 (1998).
23. Hultdin, M. et a.l Telomere analysis by fluorescence in situ hybridization and flow cytometry. *Nucleic Acids Res.* 26, 3651-3656 (1998).
24. Sasaki, K., Murakami, T., Ogino, T., Takahashi, M., Kawasaki, S. Flow cytometric estimation of cell cycle parameters using a monoclonal antibody to bromodeoxyuridine. *Cytometry* 7, 391-395 (1986).
25. Perrem, K. et al. Repression of an alternative mechanism for lengthening of telomeres in somatic cell hybrids. *Oncogene* 18, 3383-3390 (1999).
26. Guiducci, C., Cerone, M. A., Bacchetti, S. Expression of mutant telomerase in immortal telomerase-negative human cells results in cell cycle deregulation, nuclear and chromosomal abnormalities and rapid loss of viability. *Oncogene* 20, 714-725 (2001).
27. Craig, C. et al. Effects of adenovirus-mediated p16INK4A expression on cell cycle arrest are determined by endogenous p16 and Rb status in human cancer cells. *Oncogene* 16, 265-272 (1998).
28. Schmidtmayerova, H., Mayer, V. Inhibition of human immunodeficiency virus replication by azidothymidine (Azitidin Lachema) in cultured cells. *Bratisl. Lek. Listy* 94, 76-80 (1993).
29. Ostertag, E. M., Prak, E. T., DeBerardinis, R. J., Moran, J. V., Kazazian, H. H. Jr. Determination of L1 retrotransposition kinetics in cultured cells. *Nucleic Acids Res.* 28, 1418-1423 (2000).

All publications, patents and patent applications mentioned in the specification are indicative of the level of those skilled in the art to which this invention pertains. All publications, patents and patent applications are herein incorporated by reference to the same extent as if each individual publication or patent application was specifically and individually indicated to be incorporated by reference. Although the foregoing invention has been described in some detail by way of illustration and example for purposes of clarity of understanding, it will be obvious that certain changes and modifications may be practiced within the scope of the appended claims.

What is claimed is:

1. A method of treating an individual suffering from a cancer, said method comprising:
    determining that a sample comprising cancer cells from the individual are telomerase negative and show alternative lengthening of telomeres mediated by a reverse transcriptase encoded by L-1 (LINE-1) retrotransposon, and
    administering to the individual in need thereof a therapeutically effective amount of a composition comprising an inhibitor or antagonist of the reverse transcriptase,
    wherein the inhibitor or antagonist blocks said lengthening of telomeres,
    wherein said cells show telomere shortening, G2 arrest and apoptosis, and
    wherein the inhibitor or antagonist is a nucleoside analog that is at least one selected from the group consisting of: 3'-azido-2',3'-dideoxythymidine (AZT), 2',3'-dideoxyinosine (ddI) and 2',3'-didehydro-3'-deoxythymidine (d4T).

2. The method of claim 1, wherein the nucleoside analog is ddI.

3. The method of claim 1, wherein the nucleoside analog is d4T.

4. The method of claim 1, wherein the nucleoside analog is 3'-azido-2',3'-dideoxythymidine (AZT).

5. The method of claim 1, wherein the cancer is osteosarcoma, breast carcinoma, ovarian carcinoma, lung carcinoma, adrenocortical carcinoma or melanoma.

6. The method of claim 1, wherein the composition is administered orally, parenterally, subcutaneously, intramuscularly, intravascularly or topically.

7. A method for treating a cancer in a human, the method comprising:
    determining that a sample comprising cancer cells from the individual are telomerase negative and show alternative lengthening of telomeres and L-1 (LINE-1) retrotransposon encoded reverse transcriptase activity, and
    administering to the human in need thereof a therapeutically effective amount of a composition comprising one or more nucleoside analogs, or a pharmaceutically acceptable salt thereof,
    wherein said nucleoside analogs block said lengthening of telomeres,
    wherein said cells show telomere shortening, G2 arrest and apoptosis, and
    wherein said nucleoside analogs are 3'-azido-2',3'-dideoxythymidine (AZT), 2',3'-dideoxyinosine (ddI) and 2',3'-didehydro-3'-deoxythymidine (d4T).

8. The method of claim 7, wherein said nucleoside analogs are selected from the group consisting of: 3'-azido-2',3'-dideoxythymidine (AZT) and 2',3'-dideoxyinosine (ddI).

9. The method of claim 7, wherein the cancer is osteosarcoma, breast carcinoma, ovarian carcinoma, lung carcinoma, adrenocortical carcinoma or melanoma.

10. The method of claim 7, wherein the composition is administered orally, parenterally, subcutaneously, intramuscularly or intravascularly.

11. The method of claim 7, wherein a composition comprising two or more said nucleoside analogs are administered.

12. The method of claim 7, wherein the amount of one of said nucleoside analogs administered is from about 100 mg/kg of body weight to about 500 mg/kg of body weight per day.

13. A method of interfering with lengthening of telomeres in telomerase negative tumor cells in need thereof, the method comprising administering to the cells an effective amount of an inhibitor or antagonist of reverse transcriptase encoded by L-1 (LINE-1) retrotransposon in the cells wherein the inhibitor or antagonist blocks said lengthening of telomeres in said cells, and wherein the inhibitor or antagonist is a nucleoside analog, which is 3'-azido-2',3'-dideoxythymidine (AZT), 2',3'-dideoxyinosine (ddI) or 2',3'-didehydro-3'-deoxythymidine (d4T).

14. The method of claim 13, wherein the nucleoside analog is ddI.

15. The method of claim 13, wherein the nucleoside analog is d4T.

16. The method of claim 13, wherein the nucleoside analog is 3'-azido-2',3'-dideoxythymidine (AZT).

17. The method of claim 13, wherein said tumor cells are osteosarcoma, breast carcinoma, ovarian carcinoma, lung carcinoma, adrenocortical carcinoma or melanoma.

18. A method of inhibiting the growth of a telomerase negative cell in need thereof showing alternative lengthening of telomeres, the method comprising:
    contacting the cell with a nucleoside analog, wherein the nucleoside analog blocks said lengthening of telomeres,
    wherein the nucleoside analog is 3'-azido-2',3'-dideoxythymidine (AZT), 2',3'-dideoxyinosine (ddI) or 2',3'-didehydro-3'-deoxythymidine (d4T).

19. The method of claim 18, wherein the cell is contacted with AZT.

20. The method of claim 19, wherein the cell is contacted with 0.2 μM AZT.

21. The method of claim 18, wherein the cell is contacted with ddI.

22. The method of claim 18, wherein the cell is contacted with d4T.

23. The method of claim 18, wherein the telomerase negative cell is a cancer cell, wherein the cancer cell is selected from the group consisting of osteosarcoma, breast carcinoma, ovarian carcinoma, lung carcinoma, adrenocortical carcinoma or melanoma.

24. A method for interfering with Line-1 reverse transcriptase(L1RT) activity in a human cancer cell in vitro comprising providing to the human cancer cell showing alternative lengthening of telomeres induced or mediated by L1RT activity, an amount of a nucleoside analog, wherein the nucleoside analog blocks said lengthening of telomeres, and wherein the nucleoside analog is 3'-azido-2',3'-dideoxythymidine (AZT), 2',3'-dideoxyinosine (ddI) or 2',3'-didehydro-3'-deoxythymidine (d4T) administered in an amount effective to interfere with L1RT activity in the human cancer cell.

25. The method of claim 24, wherein the nucleoside analog is 3'-azido-2',3'-dideoxythymidine (AZT).

26. The method of claim 24, wherein the nucleoside analog is 2',3'-dideoxyinosine (ddI).

27. The method of claim 24, wherein the nucleoside analog is 2',3'-didehydro-3'-deoxythymidine (d4T).

* * * * *

SEQUENCE LISTING

```
<160> NUMBER OF SEQ ID NOS: 8

<210> SEQ ID NO 1
<211> LENGTH: 929
<212> TYPE: DNA
<213> ORGANISM: Homo sapiens
<220> FEATURE:
<223> OTHER INFORMATION: L1 retrotransposon nucleotides 1987 to 2915

<400> SEQUENCE: 1
atgacaggat caacttcaca cataacaata ttaactttaa atataaatgg actaaattct      60
gcaattaaaa gacacagact ggcaagttgg ataaagagtc aagacccatc agtgtgctgt     120
attcaggaaa cccatctcac gtgcagagac acacataggc tcaaaataaa aggatggagg     180
aagatctacc aagccaatgg aaaacaaaaa aaggcagggg ttgcaatcct agtctctgat     240
aaaacagact ttaaaccaac aaagatcaaa agagacaaag aaggccatta cataatggta     300
aagggatcaa ttcaacaaga ggagctaact atcctaaata tttatgcacc caatacagga     360
gcacccagat tcataaagca agtcctcagt gacctacaaa gagacttaga ctcccacaca     420
ttaataatgg gagactttaa cacccactg tcaacattag acagatcaac gagacagaaa     480
gtcaacaagg atacccagga attgaactca gctctgcacc aagcagacct aatagacatc     540
tacagaactc tccacccaa atcaacagaa tatacatttt tttcagcacc acaccacacc     600
tattccaaaa ttgaccacat agttggaagt aaagctctcc tcagcaaatg taaaagaaca     660
gaaattataa caaactatct ctcagaccac agtgcaatca aactagaact caggattaag     720
```

```
aatctcactc aaagccgctc aactacatgg aaactgaaca acctgctcct gaatgactac    780
tgggtacata acgaaatgaa ggcagaaata aagatgttct ttgaaaccaa cgagaacaaa    840
gacaccacat accagaatct ctgggacgca ttcaaagcag tgtgtagagg gaaatttata    900
gcactaaatg cctacaagag aaagcagga                                      929
```

```
<210> SEQ ID NO 2
<211> LENGTH: 30
<212> TYPE: DNA
<213> ORGANISM: Artificial Sequence
<220> FEATURE:
<223> OTHER INFORMATION: Oligonucleotide

<400> SEQUENCE: 2
ccagagattc tggtatgtgg tgtctttgtt                                      30

<210> SEQ ID NO 3
<211> LENGTH: 30
<212> TYPE: DNA
<213> ORGANISM: Artificial Sequence
<220> FEATURE:
<223> OTHER INFORMATION: Oligonucleotide sequence

<400> SEQUENCE: 3
ctttctcttg taggcattta gtgctataaa                                      30

<210> SEQ ID NO 4
<211> LENGTH: 30
<212> TYPE: DNA
<213> ORGANISM: Artificial Sequence
<220> FEATURE:
<223> OTHER INFORMATION: Oligonucleotide

<400> SEQUENCE: 4
ctcttgcttt tctagttctt ttaattgtga                                      30

<210> SEQ ID NO 5
<211> LENGTH: 30
<212> TYPE: DNA
<213> ORGANISM: Artificial Sequence
<220> FEATURE:
<223> OTHER INFORMATION: Oligonucleotide

<400> SEQUENCE: 5
cttcagttct gctctgattt tagttatttc                                      30

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide

<400> SEQUENCE: 6
tcctgctttc tcttgtaggc a                                               21

<210> SEQ ID NO 7
<211> LENGTH: 63
<212> TYPE: DNA
<213> ORGANISM: Artificial Sequence
<220> FEATURE:
<223> OTHER INFORMATION: Oligonucleotide

<400> SEQUENCE: 7
agaccatcaa gactaggaag aaactgcatc aactaatgag caaaatcacc agctaacatc     60
```

```
ata                                                              63

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide

<400> SEQUENCE: 8
atgacaggat caacttcaca c                                          21
```